US00PP26116P2

(12) United States Plant Patent
Kordes

(10) Patent No.: US PP26,116 P2
(45) Date of Patent: Nov. 24, 2015

(54) SHRUB ROSE PLANT NAMED 'KORMELAUS'

(50) Latin Name: *Rosa hybrida*
Varietal Denomination: KORmelaus

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 133 days.

(21) Appl. No.: 13/987,686

(22) Filed: Aug. 20, 2013

(51) Int. Cl.
*A01H 5/02* (2006.01)

(52) U.S. Cl.
USPC ..... Plt./104

(58) Field of Classification Search
USPC ..... Plt./104
See application file for complete search history.

(56) References Cited

PUBLICATIONS

Help Me Find: Roses, Clematis and Peonies 2015.*

* cited by examiner

*Primary Examiner* — Keith O. Robinson

(57) ABSTRACT

A new and distinct variety of rose with long lasting, novel amber yellow flowers, and attractive foliage with above average disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORmelaus'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1999. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORmelaus'.

SUMMARY OF THE INVENTION

The new rose plant may be distinguished from its seed parent, an un-named seedling, by the following combination of characteristics:

1. 'KORmelaus' has amber yellow flowers, whereas the un-named seedling has caramel yellow flowers.

2. 'KORmelaus' has a double petal count, whereas the un-named seedling has a very double petal count.

The new rose plant may be distinguished from its pollen parent, an un-named seedling, by the following combination of characteristics:

1. 'KORmelaus' has a moderately vigorous growth habit, whereas the un-named seedling has a vigorous growth habit.
2. 'KORmelaus' has above average disease resistance, whereas the un-named seedling has average disease resistance.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORmelaus' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORmelaus' was selected in May 2000 from the seedling beds to be asexually propagated for further evaluation. The first asexual propagation of 'KORmelaus' was done by budding in July 2000 at the inventor's nursery in Offenseth-Sparrieshoop, Germany.

These initial and other subsequent propagations conducted in controlled environments demonstrate that 'KORmelaus' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORmelaus' taken from plants of 3 years of age.

DETAILED BOTANICAL DESCRIPTION

The following is a description of 'KORmelaus', as observed growing in July 2013 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORgohowa', a rose variety from the same inventor described and illustrated in U.S. Plant Pat. No. 22,539 and issued on Mar. 6, 2012 are compared to 'KORmelaus' in Chart 1.

CHART 1

| Characteristic | 'KORmelaus' | 'KORgohowa' |
|---|---|---|
| Petal count | Double | Very double |
| Peduncle strength | Strong | Moderate |
| Flower buds per stem | 3 to 5 | 1 to 2 |

Parents:

*Seed parent*.—An un-named seedling.

*Pollen parent*.—An un-named seedling.

Classification:

*Botanical classification*.—*Rosa hybrida* 'KORmelaus'.

*Commercial classification*.—Shrub rose.

FLOWER AND FLOWER BUD

Blooming habit: Recurrent. Floriferous.

Flower bud:

*Size*.—Upon opening, 30 mm in length from base of receptacle to distal end of bud and 20 mm diameter at its widest point.

*Bud form*.—Short. Pointed ovoid.

*Bud color*.—As sepals first unfold, bud color is Yellow Group 13C, Red Group 46C and Orange Group 32B. When ¼ open, the upper surface of petals is Greyed-Orange Group 168D and the lower surface is Yellow-Orange Group 15C. Guard Petals are Red Group 53C.

*Sepals*.—Color: Upper surface: Yellow-Green Group 146D. Lower surface: Yellow-Green Group 146C. Intonations: Greyed-Red Group 181A on a limited number of sepals. Size: Average 25 mm (l)×8 mm (w). Shape: Weak foliaceous appendages on 3 of the five sepals. Apex: Apiculate. Base: Flat at union with receptacle. Quantity: Five. Surface texture: Upper side: Heavily pubescent. Lower surface: Lightly pubescent with limited number of stipitate glands. Margins: Light pubescence with stipitate glands present.

Flower bloom:

*Fragrance*.—Moderate.

*Duration*.—On the plant 3-5 days. As a cut flower, 2-3 days. Senesced petals drop away cleanly.

*Size*.—Medium for a shrub rose. When open, the average flower diameter is 75 mm and the average flower height is 45 mm.

*Form*.—Shape of flower when viewed from the side: Upon opening, upper part: Convex. Upon opening, lower part: Convex. Open flower, upper part: Flat. Open flower, lower part: Concave.

Color:

*Upon opening, petals*.—Outermost petals: Outer Side: Orange Group 29C with intonations of Red Group 47B. Inner Side: Greyed-Orange Group 170C with intonations of Orange Group 29B. Innermost petals: Outer Side: Red Group 37C with center stripe Yellow Group 2B. Inner Side: Orange Group 29C.

*Upon opening, basal petal spots*.—Basal petal spot, outermost petals: Outer Side: Yellow Group 3B. Inner Side: Yellow Group 3A. Basal petal spot, innermost petals: Outer Side: Yellow Group 9A. Inner Side: Yellow Group 9A.

*After opening, petals*.—Outermost petals: Outer Side: Orange Group 27A. Inner Side: Red Group 36A. Innermost petals: Outer Side: Red Group 37B with basal petal area Yellow Group 4B. Inner Side: Red Group 36A.

*After opening, basal petal spots*.—Basal petal spot, outermost petals: Outer Side: Yellow Group 3B. Inner Side: Yellow Group 3C. Basal petal spot, innermost petals: Outer Side: Green-Yellow Group 1B. Inner Side: Green-Yellow Group 1A.

General tonality.—On open flower Orange Group 29A. No change in the general tonality at the end of the 3$^{rd}$ day. Afterwards, general tonality is Orange Group 29C to Orange Group 29D.

Petals:

*Petal count*.—Double.

*Average range*.—Approximately 23-30 petals under normal conditions.

*Petal reflex*.—Petals reflex somewhat.

*Petal margin*.—Entire toe marginate.

*Petal shape*.—Obovate. Apex: Obtuse to refuse. Base: Attenuate.

*Petal size*.—30 mm (l)×25-30 mm (w).

*Thickness*.—Average.

*Petal arrangement*.—Not formal.

*Texture*.—Upper and Lower Surfaces: Smooth.

Petaloids:

*Petaloid count*.—Average of 5-8 per flower.

*Petaloid size*.—15-30 mm (l)×5-15 mm (w).

*Petaloid color*.—Inner side: Red Group 36A. Outer side: Red Group 36A.

*Petaloid texture*.—Inner and Outer Sides: Smooth.

*Margins*.—Entire to undulated.

*Petaloid shape*.—Most commonly oblanceolate. Apex: Acute. Base: Attenuate.

Reproductive organs:

*Pistils*.—Abundant. Approximately 55-60 present. Stigmas: Location: Slightly inferior in position to anthers. Color: Yellow-Orange Group 16A. Styles: Length: About 6-7 mm long. Color: Yellow-Orange Group 16C. Slight intonations of Orange-Red Group 30C.

*Stamens*.—Approximately 110-120 on average and regularly arranged. Anthers: Size: Average 3-4 mm (l)×1.5 mm (w). Color: Yellow-Orange Group 15A. Pollen: Present in limited amount. Color: Greyed-Yellow Group 161A. Filaments: Color: Yellow-Orange Group 15B. Length: 7-8 mm.

Receptacle:
- *Surface*.—Limited numbers of stipitate glands near base.
- *Color*.—Yellow-Green Group 146C.
- *Shape*.—Urn-shaped.
- *Texture*.—Smooth.
- *Size*.—10 mm (h)×7 mm (w).

Pedicel:
- *Surface*.—With stipitate glands.
- *Length*.—30-50 mm average length.
- *Diameter*.—2-3 mm average diameter.
- *Color*.—Yellow-Green Group 146D. Intonations of Greyed-Purple Group 184B.
- *Strength*.—Strong.
- *Texture*.—Smooth.
- *Borne*.—Multiple flower buds per stem, generally 3-5. Flowers held upright.

Peduncle:
- *Length*.—30-60 mm average length.
- *Diameter*.—3-4 mm average diameter.
- *Color*.—Yellow-Green Group 146B. Intonations of Greyed-Purple Group 183C.
- *Strength*.—Strong.
- *Texture*.—Smooth.

Inflorescence:
- *Type*.—Corymb.
- *Average number of flowers*.—3 to 5 flowers per inflorescence.
- *Size*.—15 cm (w)×20 to 25 cm (h).

THE PLANT

Growth: Moderately vigorous.

Plant habit: Upright to bushy. When grown as a budded field plant, the average plant height is 120 cm and the average plant width is 75 cm.

Stems:
- *Stem color*.—Young wood: Yellow-Green Group 146C. Older wood: Yellow-Green Group 146B.
- *Stem surface texture*.—Young wood: Smooth. Older wood: Rough.

Prickles: Present.
- *Incidence*.—Average of 7 per each 10 cm of stem.
- *Size*.—Average length: 5 mm.
- *Color*.—Immature prickles: Greyed-Red Group 180B. Mature prickles: Greyed-Orange Group 167A.
- *Shape*.—Deeply concave.
- *Texture*.—Smooth.

Leaves:
- *Shape*.—Compound. Normally 7 leaflets on normal leaves in middle of the stem.
- *Venation pattern*.—Pyramidal net pattern.
- *Leaf size*.—160 mm (l)×130 mm (w).
- *Abundance*.—Average.
- *Texture*.—Upper side of leaf Leathery. Under side of leaf: Leathery.

Leaflets:
- *Size*.—Average size of the terminal leaflet is 65 mm (l)×50 mm (w).
- *Shape*.—Ovate. Base: Obtuse. Apex: Acute.
- *Margins*.—Serrated.
- *Surface*.—Upper side of leaflet: Semi-glossy. Under side of leaflet: Matte.
- *Texture*.—Upper side of leaflet: Leathery. Under side of leaflet: Leathery.
- *Color, mature foliage*.—Upper Leaflet Surface: Green Group 137A. Lower Leaflet Surface: Green Group 137C.
- *Color, juvenile foliage*.—Upper Leaflet Surface: Yellow-Green Group 144A. Lower Leaflet Surface: Yellow-Green Group 146D.
- *Anthocyanin intonation*.—Greyed-Purple Group 184B. Location: Very limited on juvenile leaflets.
- *Arrangement*.—Odd pinnate.
- *Venation*.—Reticulate.

Stipules:
- *Size*.—25 mm (l)×7 mm (w).
- *Stipule color*.—Yellow-Green Group 146A.
- *Anthocyanin*.—Greyed-Red Group 181C.
- *Stipitate glands*.—Limited numbers on margin.
- *Texture*.—Smooth.
- *Shape*.—Apex: Apiculate. Base: Winged.

Petiole:
- *Length*.—Average 25 mm.
- *Diameter*. Average 3 mm.
- *Petiole color*.—Yellow-Green Group 146B. Underneath: Yellow-Green Group 146C.
- *Margins*.—With stipitate glands.
- *Prickles*.—Present on under side.
- *Texture*.—Smooth.

Petiole rachis:
- *Length*.—Average 20 mm.
- *Diameter*.—Average 2.5 mm.
- *Color*.—Yellow-Green Group 146C.
- *Margins*.—With stipitate glands.
- *Prickles*.—A few small prickles underneath.

Hips/seed formation: None observed.

Winter hardiness: To date, the variety has been grown successfully in Zone 6A-9B.

Disease resistance: Average resistance to Powdery mildew (*Sphaerotheca pannosa*) and excellent resistance to blackspot (*Diplocarpon rosae*) diseases under normal growing conditions in Jackson County, Oreg.

I claim:

1. A new and distinct variety of rose plant, as described and illustrated herein.

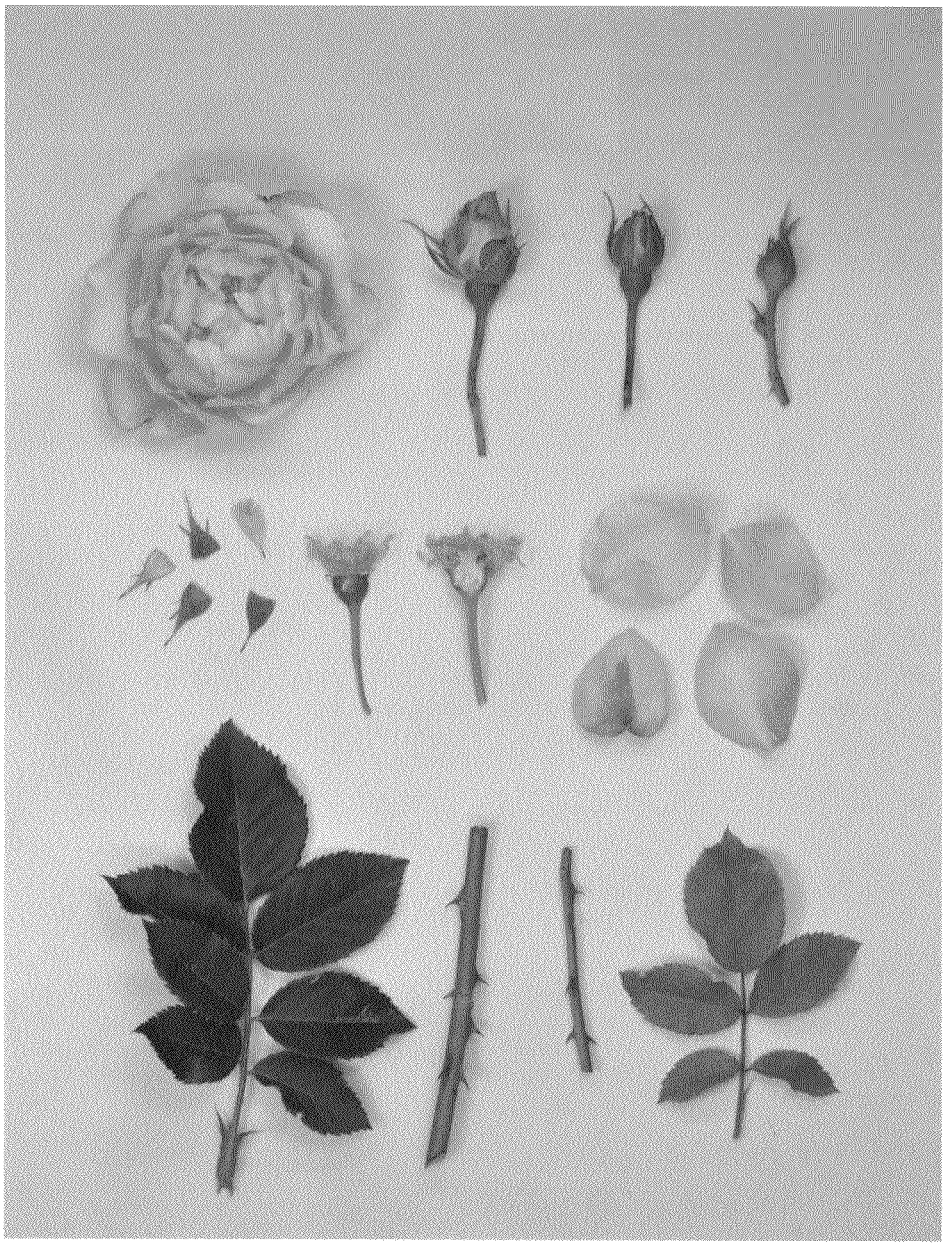

* * * * *